US010620208B2

(12) United States Patent
Wilhelm et al.

(10) Patent No.: US 10,620,208 B2
(45) Date of Patent: Apr. 14, 2020

(54) CLASSIFYING A CANCER DISEASE USING CAIX EXPRESSION (71) Applicant: WILEX AG, Munich (DE)

(72) Inventors: Olaf Wilhelm, Munich (DE); Paul Bevan, Henley-on-Thames (GB); Barbara Fall, Anzing (DE); Pia Klöpfer, Munich (DE)

(73) Assignee: Wilex AG, München (DE)

( * ) Notice: Subject to any disclaimer, the term of this patent is extended or adjusted under 35 U.S.C. 154(b) by 173 days.

(21) Appl. No.: 14/769,541

(22) PCT Filed: Feb. 21, 2014

(86) PCT No.: PCT/EP2014/053420
§ 371 (c)(1),
(2) Date: Aug. 21, 2015

(87) PCT Pub. No.: WO2014/128258
PCT Pub. Date: Aug. 28, 2014

(65) Prior Publication Data
US 2016/0002350 A1 Jan. 7, 2016

Related U.S. Application Data (60) Provisional application No. 61/829,349, filed on May 31, 2013, provisional application No. 61/768,084, filed on Feb. 22, 2013.

(51) Int. Cl.
*G01N 33/574* (2006.01)
*A61K 39/395* (2006.01)
*C07K 16/30* (2006.01)
*C07K 16/40* (2006.01)
*A61K 39/00* (2006.01)

(52) U.S. Cl.
CPC ....... *G01N 33/57438* (2013.01); *C07K 16/30* (2013.01); *C07K 16/40* (2013.01); *A61K 2039/505* (2013.01); *C07K 2317/24* (2013.01); *G01N 2333/988* (2013.01)

(58) Field of Classification Search
None
See application file for complete search history.

(56) References Cited

U.S. PATENT DOCUMENTS

| 5,981,711 | A | 11/1999 | Zavada et al. | |
|---|---|---|---|---|
| 5,989,838 | A | 11/1999 | Zavada et al. | |
| 6,004,535 | A | 12/1999 | Zavada et al. | |
| 6,093,548 | A | 7/2000 | Zavada et al. | |
| 7,354,584 | B2 * | 4/2008 | Reed | C07K 16/244 424/133.1 |
| 7,524,634 | B2 | 4/2009 | Ebert et al. | |
| 7,851,455 | B2 | 12/2010 | Harris et al. | |
| 2004/0018198 | A1 * | 1/2004 | Gudas | C07K 16/30 424/155.1 |
| 2004/0213791 | A1 * | 10/2004 | Bander | A61K 51/1072 424/155.1 |
| 2005/0158809 | A1 * | 7/2005 | Bui | G01N 33/573 435/7.23 |
| 2007/0059806 | A1 * | 3/2007 | Arnon | C12N 15/115 435/91.1 |
| 2007/0224606 | A1 * | 9/2007 | Soyupak | C12Q 1/6886 435/6.12 |
| 2008/0112960 | A1 | 5/2008 | Dorai | |
| 2011/0123537 | A1 * | 5/2011 | Wohl | C07K 16/30 424/139.1 |

FOREIGN PATENT DOCUMENTS

| EP | 0 637 336 B1 | 7/1999 |
|---|---|---|
| EP | 1 501 939 B1 | 7/2009 |
| WO | 88/08854 A1 | 11/1988 |
| WO | 93/18152 A1 | 9/1993 |
| WO | 95/34650 A2 | 12/1995 |
| WO | 00/24913 A2 | 5/2000 |
| WO | 02/062972 A2 | 8/2002 |
| WO | 02/063010 A2 | 8/2002 |
| WO | 2004/025302 A2 | 3/2004 |
| WO | 2005/037083 A2 | 4/2005 |
| WO | 2005108623 A2 | 11/2005 |
| WO | 2006002889 A2 | 1/2006 |
| WO | 2009/056342 A1 | 5/2009 |
| WO | 2011139375 A1 | 11/2011 |
| WO | 2014/128258 A1 | 8/2014 |

OTHER PUBLICATIONS

Cregger (Arch Pathol Lab Med, vol. 130, p. 1026-1030, 2006) (Year: 2006).*
He (Laboratory Investigation, vol. 91, Suppl. 1, p. 196A, Abstract 827, published Feb. 2011) (Year: 2011).*
Liao (Cancer Research, vol. 57, p. 2827-2831, 1997) (Year: 1997).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol., 79, p. 1979-1983, 1982 (Year: 1982).*
McDonald (Oncotarget, vol. 3, No. 1, p. 84-97, 2012) (Year: 2012).*
Liu et al., "Anti-renal cell carcinoma chimeric antibody G250: cytokine enhancement of in vitro antibody-dependent cellular cytotoxicity", Cancer Immunnology Immunotherapy, 2002, vol. 51, No. 3, pp. 171-177.

(Continued)

Primary Examiner — Michael Allen
(74) Attorney, Agent, or Firm — Rothwell, Figg, Ernst & Manbeck, P.C.

(57) ABSTRACT

The present invention relates to a carbonic anhydrase IX targeting compound for the use in the treatment of cancer, wherein the use comprises quantifying CAIX expression as well as the determination of a CAIX score based on the CAIX expression. The present invention relates further to a method for diagnosing, predicting and/or classifying a cancer disease comprising quantifying CAIX expression, and the determination of a CAIX score.

6 Claims, 4 Drawing Sheets
Specification includes a Sequence Listing.

(56) References Cited

OTHER PUBLICATIONS

Divgi et al., "Preoperative characterisation of clear-cell renal carcinoma using iodine-124-labelled antibody chimeric G250 (124I-cG250) and PET in patients with renal masses: a phase I trial", Lancet. Oncology, 2007, vol. 8, No. 4, pp. 304-310.
Office Action issued in the parallel Japanese application No. 2015-558463 dated Aug. 18, 2017, 7 pages.
Katja Arnold: "Press Release FDA grants Fast Track designation to Wilex's Rencarex for the adjuvant therapy of clear cell Renal Cell Carcinoma", Oct. 5, 2011 (Oct. 5, 2011), pp. 1-2, XP055110130, Retrieved from the Internet:URL:http://www.wilex.de/wp-content/uploads 2011/10/20111005 PR WILEX RENCAREX Fast-track engl.pdf [retrieved on Mar. 26, 2014].
Katja Arnold: "Press Release Wilex AG announces results of Phase III Ariser study with Rencarex in clear cell renal cell carcinoma", Oct. 16, 2012 (Oct. 16, 2012), pp. 1-3, XP055110145, Retrieved from the Internet: URL:http://www.wilex.de/wp-content/uploads/2012/10/20121016-WILEX-RENCAREX-Phase-III english.pdf [retrieved on Mar. 26, 2014] the whole document.
Arie S Belldegrun et al: "ARISER: A randomized double blind phase III study to evaluate adjuvant cG250 treatment versus placebo in patients with high-risk ccRCC-Results and implications for adjuvant clinical trials. Abstract 4507", 2013 ASCO Annual Meeting, vol. 31, Jun. 1, 2013 (Jun. 1, 2013), pp. 1-3, XP055110195, the whole document.
Katja Arnold: "Press Release—Further analysis of the ARISER study identifies a subgroup which shows significant mprovement of disease-free survival with Rencarex", Feb. 26, 2013 (Feb. 26, 2013), pp. 1-3, XP055110199, Retrieved from the Internet: URL:http://www.wilex.de/wp-content/uploads /2013/02/20130226_WILEX-RENCAREX_subgroup-analysis_english.pdf [retrieved on Mar. 26, 2014] the whole document.
Anonymous: Wilex publishes 3 Month Financial Report 2013, Apr. 11, 2013 (Apr. 11, 2013), pp. 1-24, XP055110203, Retrieved from the Internet: URL:http://www.wilex.de/pdf/Berichte/20130 411 WILEX QR 01 2013 e.pdf [retrieved on Mar. 26, 2014] pp. 2,4.
Anonymous: "Wilex—Company update German Equity Forum, Frankfurt", Nov. 1, 2013 (Nov. 1, 2013), pp. 1-24, XP055110207, Retrieved from the Internet: URL:http://www.eigenkapitalforum.com/132/p resentations/inv/WILEX AG.pdf [retrieved on Mar. 26, 2014] p. 7-p. 10.
Bui M H T et al: "Carbonic anhydrase IX is an independent predictor of survival in advanced renal clear cell carcinoma: implications for prognosis and therapy", Clinical Cancer Research, the American Association for Cancer Research, US, vol. 9, Feb. 1, 2003 (Feb. 1, 2003), pp. 802-811, XP002380265, ISSN: 1078-0432 cited in the application the whole document.
John P Kirkpatrick et al: "Elevated CAIX Expression is Associated with an Increased Risk of Distant Failure in Early-Stage Cervical Cancer", Biomarker Insights, vol. 3, Jan. 1, 2008 (Jan. 1, 2008), pp. 45-55, XP055110211, the whole document.
Zhou G X et al: "Quantification of Carbonic Anhydrase IX Expression in Serum and Tissue of Renal Cell Carcinoma Patients Using Enzyme-linked Immunosorbent Assay: Prognostic and Diagnostic Potentials", Urology, Belle Mead, NJ, US, vol. 75, No. 2, Feb. 1, 2010 (Feb. 1, 2010), pp. 257-261, XP026885551, ISSN: 0090-4295, DOI: 10.1016/J.Urology.2009.09.052 [retrieved on Dec. 5, 2009] the whole document.
Takacova et al: "Carbonic anhydrase IX is a clinically significant tissue and serum biomarker associated with renal cell carcinoma", Oncology Letters, Oct. 26, 2012 (Oct. 26, 2012), XP055110444, ISSN: 1792-1074, DOI: 10.3892/01.2012.1001 the whole document.
International Search Report cited in PCT/EP2014/053420, dated Mar. 24, 2014, 4 pages.
Atkins, Michael et al.: Carbonic Anhydrase IX Expression Predicts Outcome of Interleukin 2 Therapy for Renal Cancer; Clinical Cancer Research 2005; 11:3714-3721.
Dako RealTM Detection System, Peroxidase/DAB+ Rabbit/Mouse, Code K5001, 6th edition; Dako Corporation, Feb. 2015, 22 pgs.
McClelland A., Richard et al.: Automated Quantitation of Immunocytochemically Localized Estrogen Receptors in Human Breast Cancer; Cancer Research 50, 3545-3550, Jun. 15, 1990.
Murri-Plesko, Margarita T. et al.: Antibody inhibiting enzymatic activity of tumour-associated carbonic anhydrase isoform IX; European Journal of Pharmacology 657 (2011) 173-183.
Opaysky, Rene et al.: Human MN/CA9 Gene, a Novel Member of the Carbonic Anhydrase Family: Structure and Exon to Protein Domain Relationships; Genomics 1996, 33, pp. 480-487.
Svastova, Eliska et al.:Hypoxia activates the capacity of tumor-associated carbonic anhydrase IX to acidify extracellular pH; FEBS Letters 577 (2004); pp. 439-445.
Wykoff C., Charles et al.:Hypoxia-inducible Expression of Tumor-associated Carbonic Anhydrases; Cancer Res., Mar. 2000, 60:7075-7083.
Wilex: Instructions for use CA IX IHC Kit (35 tests) Item No. 06490035 for in Vitro Use, 5, May 2012, 14 pages.
Katja Arnold: "Press Release Wilex AG announces results of Phase III ARISER study with Rencarex in clear cell renal cell carcinoma", Oct. 16, 2012 (Oct. 16, 2012), pp. 1-3, XP055110145, Retrieved from the Internet: URL:http://www.wilex.de/wp-content/uploads/2012/10/20121016-WILEX-RENCAREX-Phase-III englishl.pdf [retrieved on Mar. 26, 2014] the whole document.
Katja Arnold: "Press Release—Further analysis of the ARISER study identifies a subgroup which shows significant improvement of disease-free survival with Rencarex", Feb. 26, 2013 (Feb. 26, 2013), pp. 1-3, XP055110199, Retrieved from the Internet: URL:http://www.wilex.de/wp-content/uploads /2013/02/20130226_WILEX-RENCAREX_subgroup-analysis_english.pdf [retrieved on Mar. 26, 2014] the whole document.
Anonymous: 113-Month Financial Report 2013, Apr. 11, 2013 (Apr. 11, 2013), pp. 1-24, XP055110203, Retrieved from the Internet: URL:http://www.wilex.de/pdf/Berichte/20130 411 WILEX QR 01 2013 e.pdf [retrieved on Mar. 26, 2014] pp. 2,4.
Silvia Pastorekova: "Carbonic anhydrase IX is a clinically significant tissue and serum biomarker associated with renal cell carcinoma", Oncology Letters, Oct. 26, 2012 (Oct. 26, 2012), XP055110444, ISSN: 1792-1074, DOI: 10.3892/01.2012.1001 the whole document.
Bleumer et al., "A phase II trial of chimeric monoclonal antibody G250 for advanced renal cell carcinoma patients", British Journal of Cancer, (2004) 90, 985-990.
English translation of Notice of Last Non-Final Rejection cited in Korean Application No. 10-2015-7025649 dated Aug. 25, 2019, 9 pages.

\* cited by examiner

Figure 1

| CAIX Cut-off | | ITT | PP |
|---|---|---|---|
| >2.0 | HR | 0.78 | 0.70 |
| | p-value | 0.137 | 0.049 |
| | sample size | 362 | 332 |
| | DFS events | 145 | 127 |
| >2.1 | HR | 0.80 | 0.70 |
| | p-value | 0.196 | 0.058 |
| | sample size | 322 | 296 |
| | DFS events | 130 | 114 |
| >2.2 | HR | 0.73 | 0.65 |
| | p-value | 0.094 | 0.031 |
| | sample size | 291 | 268 |
| | DFS events | 117 | 103 |
| >2.3 | HR | 0.74 | 0.63 |
| | p-value | 0.142 | 0.043 |
| | sample size | 234 | 213 |
| | DFS events | 94 | 82 |
| >2.4 | HR | 0.77 | 0.67 |
| | p-value | 0.253 | 0.098 |
| | sample size | 200 | 184 |
| | DFS events | 80 | 72 |
| >2.5 | HR | 0.64 | 0.55 |
| | p-value | 0.078 | 0.030 |
| | sample size | 166 | 153 |
| | DFS events | 65 | 59 |
| >2.6 | HR | 0.54 | 0.48 |
| | p-value | 0.040 | 0.019 |
| | sample size | 117 | 107 |
| | DFS events | 51 | 47 |

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Leu Ser Thr Ala Phe Ala Arg Val
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Ala Leu Gly Pro Gly Arg Glu Tyr Arg Ala Leu
1               5                   10
```

CLASSIFYING A CANCER DISEASE USING CAIX EXPRESSION

CROSS REFERENCE TO RELATED APPLICATION

This application is a 35 U.S.C. 371 National Phase Entry Application from PCT/EP2014/053420, filed Feb. 21, 2014, which claims the benefit of U.S. Patent Application Nos. 61/768,084 filed on Feb. 22, 2013 and 61/829,349 filed on May 31, 2013, the disclosures of which are incorporated herein in their entirety by reference.

The present invention relates to a carbonic anhydrase IX targeting compound for the use in the treatment of cancer, wherein the use comprises quantifying CAIX expression as well as the determination of a CAIX score based on the CAIX expression. The present invention relates further to a method for diagnosing, prognosing and/or classifying a cancer disease comprising quantifying CAIX expression, and the determination of a CAIX score.

The transmembrane protein carbonic anhydrase IX (CAIX) is a member of the large family of carbonic anhydrase enzymes which share the ability to catalyze the reversible hydration of carbon dioxide to carbonic acid, leading to a decrease in pH (Opaysky R, et al., Genomics 1996, 33: 480 487). Up-regulation of CAIX gene expression occurs in response to hypoxia via direct transcriptional activation by hypoxia inducible factor-1 alpha (HIF-1α), and is believed to be involved in sensing and maintaining the acidic environment of hypoxic cells, particularly within the hypoxic regions of tumors (Wykoff et al., Cancer Res 2000, 60: 7075-708; Svastova et al., FEBS Letters 2004 577: 439-445.)

The G250 antigen is closely associated with numerous carcinomas such as renal cell carcinoma. The G250 antigen was first described as a kidney cancer-associated antigen (WO 88/08854). Later, it was found to be identical with the tumor-associated antigen MN, a cell surface antigen with carbonic anhydrase activity, also referred to as CAIX.

Normal CAIX expression is found in gastric, intestinal and biliary mucosa, where its physiological role resides in pH regulation. Besides its normal expression pattern, CAIX expression is found in a variety of tumors including cervical, esophageal, colorectal, lung, pancreas, biliary and renal cell clear cell carcinomas (RCC).

Antibodies against CAIX, therefore, can be employed for cancer therapy. Anti-G250 antibodies are described, for example, in EP 637 336, WO 93/18152, WO 95/34650, WO 00/24913, WO 02/063010, WO 04/025302, WO 05/037083, WO 2011/139375 and foreign counterparts thereof. Further, WO 02/062972 describes a hybridoma cell line DSM ACC 2526 which produces the monoclonal antibody G250. The monoclonal antibody G250 recognizes an antigen preferably expressed on membranes of renal cell carcinoma cells (RCC), but not expressed in normal proximal tubular epithelium. The G250 antibody binds to the antigen G250, which is also called MN antigen (cf., for example, WO 93/18152) or CAIX (carbonic anhydrase IX).

Methods for determining CAIX expression are known to a person skilled in the art and include but are not limited to immunohistochemical staining of tissue sections which are e.g. described in Bui et al., Clinical Cancer Research 2003, 9: 802-811, Atkins et al., Clin. Cancer Res 2005, 11: 3714-3721, U.S. Pat. Nos. 5,989,838, 6,004,535, 6,093,548, 7,524,634, 7,851,455. Such methods may be used in human renal clear cell carcinoma prognosis.

It was the object of the present invention to provide methods, which make it possible to characterise a CAIX-associated cancer disease further and predict how efficient or successful treatment with a CAIX targeting compound would be. According to the present invention, this object is achieved by the definition of a novel CAIX score and its use in the treatment, diagnosis, prognosis and classification of cancer.

Thus, a first aspect of the present invention relates to a carbonic anhydrase IX (CAIX) targeting compound for use in the treatment of cancer, wherein the use comprises quantifying CAIX expression in at least one tumor sample provided from a subject to be treated, determining a CAIX score based on the CAIX expression in the tumor sample, and the subject is treated if a predefined CAIX score is reached. Thus, the cancer to be treated is characterised by a predefined CAIX score.

In terms of the present invention the CAIX score is preferably determined, or calculated respectively, on the basis of CAIX expression described by a combination of tumor cell extent and staining intensity. In other words, the amount/percentage of CAIX antigen expressing tumor cells as well as the staining intensity of the stained tumor cells are both considered in the CAIX score used herein. The CAIX expression can be considered to be a measure of the antigen density preferably a measure of the CAIX polypeptide density within the tumor tissue of the patient suffering from the cancer to be treated preferably wherein the cancer is RCC or ccRCC. The CAIX score is a value describing the amount of immunoreactivity of a marker such as CAIX in a sample. The score considers both staining intensity and the percentage of cells stained at a specific range of intensities. The score is determined by summing the products of the percentage cells stained at a given staining intensity (0-100) in a sample (such as a tissue section of a ccRCC cancer) and the staining intensity (0-3). Preferably the score can be rendered for a specific compartment for example cytoplasm, membrane, nucleus. A score can also be determined utilizing a numeric scale of 0-4 for the staining intensity. The score than is in the range of 0 to 400 instead of 0 to 300 in the case of a score with a staining intensity of 0-3 (McClelland et al., Cancer Res. 50:3545-3550, 1990).

In particular, the CAIX score is determined and/or calculated by the Formula CAIX score=(0×percentage of viable tumor cells with no staining intensity)+(1×percentage of viable tumor cells with faint perceptible staining intensity)+(2×percentage of viable tumor cells with moderate staining intensity)+(3×percentage of viable tumor cells with strong staining intensity). For example, a sample with 10% staining intensity of 1, 20% staining intensity of 2 and 20% of staining of 3 and 20% of unstained cells have a score of (1×10)+(2×20)+(3×20)+(0×50)=110 or if calculated (1×10/100)+(2×20/100)+(3×20/100)+(0×50/100)=1.1.

The CAIX score can take any value between 0 (no staining) and 300 (100% viable tumor cells with an intensity scaling of 3+) or 0 and 3 preferably between 0.0 and 3.0.

In the context of the present invention "tumor cell extent" or the amount of CAIX antigen expressing tumor cells is considered in the CAIX score formula according to the present invention by the indication of the percentage rate of viable tumor cells and their staining intensity. The viable tumor cells may be counted or determined by methods known to a person skilled in the art. For example, the number of cells and/or the respective percentage rate may be determined by visual counting or computer-assisted programs such as an automatic imaging system.

Tumor cell extent as part of the CAIX score is graded into a four-tired scaling factor (0, 1+, 2+ and 3+). The scaling factor 0 is derived from the CAIX staining comparable to control samples and represents lack of CAIX expression. The scaling factors 1+ to 3+ are derived from an average sample of tumor cells expressing CAIX, which show tumor cell staining from barely perceptible to strong. Usually a histologist or pathologist of average skill in the art can make the classification by conventional analysis by eye (Cregger et al., Arch. Pathol. Lab. Med., 2006, 130: 1026-1030). The absolute value of staining intensity may depend, e.g., on the applied staining reagent, the tumor tissue to be stained, etc. However, inter alia, this problem can be overcome by using the above scaling system comprising grades+1 to +3.

The staining intensity in tumor cells increases almost proportionally from barely perceptible staining to strong staining. Along this linear increase of staining intensity the tumor cells expressing CAIX are divided into three groups having a scaling from 1+ to 3+, with the respective increase in staining intensity being the same for each group. In other words, the viable tumor cells are separated into cells with faint or barely perceptible staining intensity (scaling 1+), moderate staining intensity (2+) and strong staining intensity (3+).

Once a score system has been established for a specific staining agent and specific tumor cells in an average sample of tumor cells defining a reference system, it can be used for further samples of tumor cells, i.e. the respective CAIX score system does, of course, not have to be established for each sample of tumor cells.

"Staining intensity" according to the present invention means the percentage of tumor cells within each of the four-tired scaling factor. The percentage can be any between 0% and 100%. The intensity of staining is determined as a percentage of tumor cells displaying faint or barely perceptible membrane staining for scaling+1, as a percentage of tumor cells displaying moderate membrane staining for scaling+2, as a percentage of tumor cells displaying moderate membrane staining for scaling+3 for each tissue sample (Table 1).

TABLE 1

| Staining intensity | Scaling |
|---|---|
| % of tumor cells displayed faint/barely perceptible membrane staining | 1+ |
| % of tumor cells displayed moderate membrane staining | 2+ |
| % of tumor cells displayed strong membrane staining | 3+ |

The classification of tumor cells expressing CAIX in the respective scaling group can easily be made by comparing the staining intensity of the sample with the reference tumor sample on which the CAIX scoring system was based. Thus, it is possible that samples of tumor cells do not include all three scaling groups.

A person of average skill in the art knows methods for determining staining intensity, either for defining a score system or for comparing different samples of cells or classifying cells into a score system for the purpose of comparing the staining intensity (cf. Cregger et al., 1026, Arch. Pathol. Lab. Med., vol. 130, July 2006). The determination of the staining intensity or the classification into a score system may be carried out manually or via a computer-assisted program or any other suitable method. In a preferred embodiment, the score system is applied using standardized control tumor assays in combination with a device that provides quantitative and objective output.

An example for calculating the CAIX score for 100% CAIX antigen extent expression with 40% moderate and 60% strong staining intensity will be shown in the following. Further examples for different extents of CAIX expression, a different content of staining intensity and the respective scores are shown in Table 2.

Calculation of CAIX Score:

100% CAIX antigen extent expression with 40% moderate & 60% strong staining intensity $$(1*(0/100))+(2*(40/100))+(3*(60/100))$$

$$0+0.8+1.8=2.6$$

TABLE 2

| extent CAIX expression | 1+ | 2+ | 3+ | Score |
|---|---|---|---|---|
| 100 | 0 | 40 | 60 | 2.60 |
| 100 | 10 | 60 | 30 | 2.20 |
| 100 | 5 | 25 | 70 | 2.65 |
| 100 | 50 | 30 | 20 | 1.70 |
| 100 | 0 | 10 | 90 | 2.90 |
| 10 | 0 | 100 | 0 | 0.20 |
| 10 | 100 | 0 | 0 | 0.10 |
| 50 | 100 | 0 | 0 | 0.50 |
| 50 | 30 | 30 | 40 | 1.05 |
| 50 | 50 | 30 | 20 | 0.85 |
| 50 | 20 | 70 | 10 | 0.95 |
| 50 | 70 | 20 | 10 | 0.70 |

According to the present invention the CAIX score is based on the CAIX expression which has to be determined. Herein, the terms CAIX expression and CAIX protein expression can be used interchangeable. Preferably, the term CAIX expression is related to the amount of CAIX protein expressed. Thus, a further aspect of the present invention relates to a CAIX targeting compound for use in the treatment of cancer, wherein the use comprises quantifying CAIX protein in at least one tumor sample provided from a subject to be treated determining a CAIX score-based on the CAIX protein in the tumor sample and the subject is treated if a predefined CAIX score is reached.

Another aspect of the present invention relates to a carbonic anhydrase IX (CAIX) targeting compound for use in the treatment of cancer comprising administering a therapeutically effective amount of a CAIX antagonist to the patient if the patient's cancer has been found to have a CAIX score of equal to or greater than 2.0, 2.1, 2.2, 2.3, 2.4, 2.5 or 2.6. In a preferred embodiment, the CAIX score is equal to or greater than 200, 210, 220, 230, 240, 250 or 260, most preferably the CAIX score is equal to or greater than 260.

A further embodiment of the present invention relates to a carbonic anhydrase IX (CAIX) targeting compound for use in the treatment of cancer whereby at least one tumor tissue sample of the subject to be treated is characterized by a CAIX score of at least 2.0, 2.1, 2.2, 2.3, 2.4, 2.5 or 2.6, more preferably of at least 200, 210, 220, 230, 240, 250 or 260, most preferably of at least 260.

Thereby expressed CAIX is quantified, if any, present in one or more samples derived from a subject to be treated. Preferably, the sample derived from the subject to be treated is a tissue sample of the cancer to be treated. More preferably the tissue sample of the cancer to be treated is a tissue sample derived from the renal cell carcinoma (RCC), most preferably from the renal clear cell carcinoma (ccRCC).

Preferably, expressed CAIX is quantified by tumor cell staining, preferably immunohistochemical staining, more preferably immunohistochemical staining wherein CAIX protein or CAIX polypeptide is specifically bound by a monoclonal antibody, more preferably by a monoclonal antibody with an epitope binding domain at the N-terminus of CAIX, even more preferably by the monoclonal antibody M75, most preferably by the monoclonal antibody that is secreted from the hybridoma VU-M75 which has accession No. ATCC HB 11128. A person skilled in the art knows suitable methods of immunohistochemical staining methods. Kits for immunohistochemical staining are commercially available and include but are not limited to the CAIX IHC Kit offered by Oncogene Science 100 Acorn Park Drive, Cambridge, Mass. 02140, USA. Another example for a method of immunohistochemical staining is, e.g., described in EP 1 501 939 B1. Immunohistochemical staining of tissue sections can be done with anti-CAIX antibody using a peroxidase technique with antigen retrieval using heat treatment as described by Dako staining systems (Dako Corporation, Carpenteria, Calif.). The antibodies used in the immunoassay and/or immunohistochemical staining may be polyclonal or monoclonal. Preferably, monoclonal antibodies are used. In the method of immunohistochemical staining according to the present invention labelled or unlabelled antibodies may be used. Labelled detection means including labels that may comprise fluorescent means, enzymes, co-enzymes, radionucleotides, chemiluminescent means, enzyme substrates, particles, dyes, etc. The respective assays include enzyme immunoassays, fluorescent immunoassays, radioimmunoassays, ELISAS, etc. Detection antibodies of use in the immunohistochemical staining tissue include monoclonal antibodies M75, MN9, MN, 12, MN7. A detection antibody that is preferably used according to the present invention is M75. The M75 antibody is further described in U.S. Pat. No. 5,981,711 and is part of the CAIX IHC Kit offered by Oncogene Science (see supra). Particularly preferred are staining methods which provide measurable and/or comparable results such as dye intensity, fluorescent intensity, radio signals, enzyme activity, etc.

According to a preferred embodiment, the expressed CAIX comprises a CAIX polypeptide or fragment of CAIX polypeptide. According to another preferred embodiment, the expressed CAIX comprises an mRNA that encodes a CAIX polypeptide or fragment of CAIX polypeptide. A person skilled in the art knows methods to determine the amount of mRNA in the sample of a cell, such as Northern Blot, microassays, real-time PCR etc.

According to a preferred embodiment, the subject is to be treated if the CAIX score in the tumor sample provided from the subject is ≥2.0 preferably from a subject at an age of less than 65 years. In a further, more preferred embodiment, the score is ≥2.1, more preferably ≥2.2, more preferably ≥2.3, even more preferably ≥2.4, even more preferably ≥2.5. An analysis for all possible CAIX scores from 0.0 to 3.0 reveals that the more the CAIX score increases the more significant the treatment effect is. The patients having a CAIX score of ≥2.6 show a statistically significant treatment effect when treated with a CAIX targeting compound, in particular an anti-G250 antibody. Thus, a CAIX score ≥2.6 is regarded as the most preferred embodiment. Preferably the tumor sample provided from the subject is at least one tissue sample of the cancer of the subject to be treated. More preferably the tumor sample provided from the subject is at least one tissue sample derived from the renal cell carcinoma (RCC) of the subject to be treated, most preferably from the renal clear cell carcinoma (ccRCC).

According to a further preferred embodiment, the CAIX score or predefined CAIX score is equal or greater than 2.0, 2.1, 2.2, 2.3, 2.4, 2.5 or 2.6. In some embodiments, the CAIX score is equal to or greater than 200, 210, 220, 230, 240, 250 or 260. In a preferred embodiment, the CAIX score is equal to or greater than 260.

The CAIX targeting molecule may be any compound, specifically recognising CAIX mediating its activity by binding to CAIX or a fragment or splice variant thereof; irreversibly binding at the entrance to the active site, and/or inhibiting CAIX by coordinating to the zink ion at the active site of CAIX. Preferably the CAIX targeting compound specifically interacts with a CAIX polypeptide. Specifically interacting with (e.g. recognising or binding to) means that the CAIX targeting compound e.g. antibody has a greater affinity to CAIX than to other polypeptides. In one embodiment the CAIX targeting compound interacts with (i.e. binds to or recognizes) or modulates the activity of CAIX polypeptide and/or mediates an antibody dependent cell cytotoxicity (ADCC) and/or complement mediated cytotoxicity (CDC). Thus, according to one embodiment, the targeting compound is a CAIX inhibitor. Said CAIX inhibitor may act on the protein level or the nucleic acid level. Examples for CAIX inhibitors e.g. acting on the protein level include but are not limited to peptides and anti-CAIX antibodies as well as functional fragments of those antibodies or small organic molecules, preferably having a molecular weight below 500 g/mol. Examples of anti-CAIX antibodies or antibodies against CAIX are described in EP 637 336, WO 93/18152, WO 95/34650, WO 00/24913, WO 02/063010, WO 04/025302, WO 05/037083, WO 2011/139375, Murri-Plesko et al., Eur J Pharmacol 2011, 657: 173-183. Examples of small organic molecules include but are not limited to sulphonamides, heteroaromatic sulphonamides, sulfamates, coumarins and thiocoumarins and BAY-79-4620. Examples for inhibitors acting on the nucleic acid level are siRNA molecules, ribozymes and/or antisense molecules.

According to an especially preferred embodiment, the CAIX targeting compound and/or inhibitor is an anti-CAIX antibody and/or functional fragment of such an antibody. According to a preferred embodiment, the fragment of the anti-CAIX antibody has essentially the same CAIX-binding and/or inhibiting activity as the full-length anti-CAIX antibody and/or is an epitope-binding fragment of the anti-CAIX antibody.

In another preferred embodiment, the antibody or/and the antibody fragment thereof is selected from the group consisting of polyclonal antibodies, monoclonal antibodies, antigen-binding fragments thereof such as F(ab').sub.2, Fab', sFv, dsFv and chimerized, humanized and fully human variants thereof. According to a further preferred embodiment, this anti-CAIX antibody or epitope-binding fragment thereof binds to the amino acid sequence LSTAFARV (SEQ ID NO: 1) and/or ALGPGREYRAL (SEQ ID NO: 2).

According to a further particularly preferred embodiment, the CAIX targeting compound is the antibody anti-G250 and/or an epitope-binding fragment thereof. Anti-G250 antibodies are, e.g., described in EP-B-0 637 336. It is particularly preferred that the anti-tumor antibody is chimeric or humanised G250 antibody and/or a fragment thereof. The antibodies for use in the present invention may be produced by any suitable method known in the art including but not limited by methods as described in PCT/EP02/01282 and PCT/EP02/01283, which are incorporated herein by reference.

An especially preferred antibody is cG250, preferably girentuximab (INN). Another especially preferred embodiment is the monoclonal antibody G250 produced by the hybridoma cell line DSM ACC 2526. The antibody cG250 is an IgG1 kappa light chain chimeric version of an originally murine monoclonal antibody mG250.

The cancer to be treated is a cancer which is characterised by expressing CAIX. In particular, the cancer is characterised by having a CAIX score as defined herein ≥2.0, preferably from a subject at an age of less than 65 years, and in particular having a CAIX score ≥2.6 as set out above. According to an especially preferred embodiment the subject to be treated is at an age of less than 65 years and has a CAIX score ≥2.6.

Preferably, the cancer or patient's cancer is selected from the group comprising cervical carcinomas, esophageal carcinomas, gastric carcinomas, colorectal carcinomas, ovarian carcinomas, liver carcinomas, bladder carcinomas, lung carcinomas, head and neck cancer, billary carcinomas, and renal cell carcinomas.

In a particularly preferred embodiment the cancer is renal clear cell carcinoma (RCC).

In the most preferred embodiment of the present invention renal clear cell carcinoma is treated by administering the antibody G250, and in particular cG250, preferably girentuximab.

It is preferred that the subject to be treated has been diagnosed with a non-metastatic type of cancer or non-metastatic disease, more preferably with a non-metastatic type of cancer or non-metastatic disease or/and has to be diagnosed as having a high risk of recurrence.

According to a further embodiment, the CAIX targeting compound, and in particular the anti-G250 antibody, is to be used after the subject to be treated has undergone a primary tumor resection, preferably a tumor nephrectomy, more preferably a tumor nephrectomy and lymphadenectomy. Preferably, this primary tumor is a G250 antigen-expressing tumor, particularly selected from the group of cervical carcinomas, esophageal carcinomas, gastric carcinomas, colorectal carcinomas, liver carcinomas, bladder carcinoma, lung carcinomas, billary carcinomas, head and neck cancer and renal clear cell carcinoma (ccRCC).

Accordingly, in a further preferred embodiment the CAIX targeting compound, and in particular the anti-G250 antibody, is used as an adjuvant therapy. In terms of the present invention, adjuvant therapy describes a way to target any remaining cancer cells that cannot be seen. Adjuvant therapies are usually used after primary treatments such as surgery or radiation to guard any cancer recurrences. An example of adjuvant therapy is the additional treatment usually given after surgery where all detectable disease has been removed, but where there remains a statistical risk of relapse due to occult disease. Types of adjuvant therapy comprise chemotherapy, hormone therapy, radiation therapy and/or immunotherapy. For example, radiotherapy or systemic therapy is commonly given as adjuvant treatment after surgery for breast cancer. Systemic therapy may consist of chemotherapy, immunotherapy or biological response modifiers or hormone therapy. Preferably, if the CAIX targeting compound according to the present invention is used, an adjuvant therapy may be combined with any of these types of known adjuvant therapies.

A further aspect of the present invention relates to a CAIX targeting compound for use in the treatment of cancer expressing CAIX, wherein cancer cells are characterised by a CAIX score ≥2.0, and in particular ≥2.6. Of course, any CAIX targeting compound as specified above can be used.

Preferably, the CAIX targeting compound is an anti-G250 antibody, in particular cG250 antibody, and/or an epitope-binding fragment thereof.

According to a further embodiment, the CAIX targeting compound, and in particular the antibody cG250, is for the use and in the treatment of renal clear cell carcinoma having a CAIX score ≥2.0 and in particular ≥2.6. According to another embodiment, the CAIX targeting compound, and in particular the antibody cG250, is for the use and in the treatment of renal clear cell carcinoma having a CAIX score ≥2.0 and wherein the subject to be treated is less than 65 years of age and/or having a CAIX score of ≥2.6.

A further aspect of the present invention relates to a method for diagnosing, prognosing and/or classifying a cancer disease comprising
(a) quantifying the expression of CAIX in a cancer sample by staining and
(b) classifying the cancer disease according to the extent and staining intensity of stained cancer cells.

The method of diagnosing may further comprise the determination of a CAIX score as described above.

The cancer to be diagnosed and/or classified is preferably a cancer as described above, and particularly renal clear cell carcinoma. Preferably, this cancer has a CAIX score ≥2.0, and even more preferably ≥2.6.

The prognosis embodiment includes the use of the CAIX score to predict whether a patient to be treated would respond to treatment with a CAIX targeting compound or not, in particular to treatment with an anti-G250 antibody. It is particularly used to predict if a patient would respond to treatment with the cG250 antibody, preferably with girentuximab. In other words it can be prognosed which patients will probably benefit from a treatment with CAIX targeting compounds. For example, patients having renal clear cell carcinoma, wherein the corresponding tumor cell sample shows a CAIX score ≥2.6 will most probably benefit from a treatment with the cG250 antibody, preferably girentuximab.

Patients with a high T-stage (T3/T4), a low grading (G1/G2), no lymph node involvement (N0/NX) and no metastatic disease (M0) have a worse prognosis with a low CAIX score as compared to patients with a high CAIX score.

A further aspect of the present invention relates to a method for treating cancer, said method comprising
(a) defining the expression of a CAIX in a cancer cell obtained from a subject to be treated by staining,
(b) determining a CAIX score according to the extent and staining intensity of the cancer cells and
(c) administering a CAIX targeting compound if in step (b) a predefined CAIX threshold value has been exceeded.

According to a preferred embodiment, the CAIX targeting compound of the present invention, and in particular the anti-G250 antibody, is administered as monotherapy protocol, preferably is administered as a monotherapy.

The CAIX targeting compound, and in particular the anti-G250 antibody, preferably the cG250 antibody, more preferably girentuximab may also be administered in a combination therapy protocol or as a combination therapy, e.g., as already outlined above, an adjuvant anti-G250 antibody treatment may be combined with any other type of adjuvant therapy. Preferably, a cytokine may be co-administered together with the antibody to increase antibody-dependent cellular cytotoxicity (ADCC) and/or to activate the immune system of the patient, e.g., the NK cells. This cytokine is preferably selected from the group consisting of interleukins such as IL-2, -3, -4, -5, -6, -7, -8, -9, -10, -12, -13, -14, and -15, interferon, e.g., IFN-α, IFN-β, and IFN-γ, TFN-α, TNF-β, nerve growth factor, ligands of CD40, Fas, CD27 and CD30, macrophage-inhibiting protein, Rantes, active fragments of pharmaceutically acceptable analogues and derivatives, and mixtures thereof. More preferably, the cytokine is selected from IL-2 and IFN-α. Of course, a combination with further cytotoxic means, e.g, doxorubicin, cis-platin or carboplatin and other neoplastic means, is possible.

The artisan of ordinary skill can determine the dosage of the CAIX targeting compound used, and in particular G250-antigen-specific antibody, based on age, weight, condition and the severity of the disease, for example. A dosing regimen of either 20 mg or 50 mg cG250 antibody, for example, per patient on a weekly cycle, will deliver concentrations above 0.5 μg/ml preferably 1 μg/ml and therefore should be adequate for efficacy. Therefore, in a preferred embodiment a weekly dose of the G250-specific antibody of 5-250 mg/week, more preferably 10-100 mg/week, and most preferably 20 mg/week to 50 mg/week are administered.

According to a preferred embodiment, the G250 antigen-specific antibody and/or antibody fragment thereof is administered to a subject in need thereof in at least two treatment stages in which different, preferably decreasing amounts of the antibody are administered.

It is more preferred that the method of the present invention comprises the administration of a G250-antigen-specific antibody or/and an antibody fragment thereof to a subject in need thereof in two stages, wherein
(a) a dose of 10-250 mg/week, preferably 20-100 mg/week, more preferably 30-100 mg/week, even more preferably 30-55 mg/week and most preferably 50 mg/week of the G250-antigen-specific antibody is administered in the first treatment stage and
(b) a dose of 5-100 mg, preferably 10-50 mg, more preferably 15-25 mg, most preferably 20 mg/week of the G250-antigen-specific antibody is administered in the second treatment stage.

It is even more preferred that the first treatment stage comprises administration of 50 mg/week of the G250-specific antibody, and the second treatment stage comprises administration of 20 mg/week.

The antitumor antibody is preferably administered intravenously, preferably by infusion or intravenous injections. The administration of the antibody by infusion is preferably performed in up to about 30 minutes, more preferably in about 15 minutes. Of course, the CAIX targeting compound can also be applied intraperitoneally or intramuscularly.

Dosing schemes with weekly infusions of either 20 or 50 mg of cG250 antibody for up to 20 weeks appear to be well tolerated and do not lead to significant HACA development.

It is therefore preferred that the first treatment stage comprises up to 12 weeks, preferably up to 6 weeks, even more preferably up to one week and the second treatment stage comprises up to 156 weeks, preferably up to 104 weeks, more preferably up to 52 weeks, even more preferably up to 12-24 weeks.

In the most preferred embodiment, the first treatment stage comprises up to one week and the administration of a single loading dose of 50 mg/week of cG250 antibody, and the second treatment stage comprises up to 24 weeks and the administration of 20 mg/week of cG250 antibody for the treatment of renal clear cell carcinoma.

In a further preferred embodiment, the first treatment stage comprises up to one week and the administration of a single loading dose of 50 mg/week of cG250 antibody intravenously, and the second treatment stage comprises up to 24 weeks and the administration of 20 mg/week of cG250 antibody for the treatment of renal clear cell carcinoma, preferably the second treatment stage comprises at least 8 consecutive intravenous administration of 20 mg/week of cG250 antibody for the treatment of renal clear cell carcinoma.

The CAIX targeting compound, in particular the cG250 antibody, may, of course, be administered in a pharmaceutical composition. This pharmaceutically acceptable composition may comprise acceptable carriers, diluents and/or adjuvants. The term "carrier" when used herein includes carriers, excipients and/or stabilisers that are non-toxic to the cell or mammal being exposed thereto at the dosages and concentrations employed. Often the physiologically acceptable carriers are aqueous pH buffered solutions or liposomes. Examples of physiologically acceptable carriers include buffers such as phosphate, citrate and other organic acids; anti-oxidants including ascorbic acid, low molecular weight (less than about 10 residues) polypeptides; proteins such as serum albumin, gelatine or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins, gelating agents such as EDTA, sugar, alcohols such as mannitol or sorbitol; salt-forming counterions such as sodium; and/or non-ionic surfactants such as TWEEN, polyethylene or polyethylene glycol.

In an especially preferred embodiment the CAIX targeting compound is administered in normal saline (0.9% sterile sodium chloride in water).

According to an especially preferred embodiment, the antibody cG250 is administered in normal saline by intravenous infusion, e.g., 100 ml solution over 15 min.

The term "carbonic anhydrase IX" and "CAIX", "CA9", "MN" and "G250" are herein considered to be synonymous.

"cG250" and girentuximab are used interchangeable.

"Antigen" refers to a ligand that can be bound by e.g. an antibody. The portions of the antigen that makes contact with the antibody are denominated "epitopes".

If not mentioned otherwise, "staining" as used herein refers to any method which makes tumor cells visible. A preferred "staining" method is immunohistochemical staining as described above.

EXAMPLES

The following results are based on a randomised double blind Phase III study to evaluate adjuvant cG250 treatment versus placebo in patients with renal clear cell carcinoma (ccRCC) and high risk of recurrence.
Objectives:
The objectives in this study were to evaluate disease free survival (DFS) on girentuximab therapy as compared to placebo and to evaluate overall survival (OS) on girentuximab therapy as compared to placebo.

Patients:

864 patients (ITT) were enrolled in a prospective, two armed, randomized, double blinded, placebo controlled study. The evaluation of the disease free survival was assessed by an independent Radiological Review Committee. 855 patients received at least one study treatment (cG250 or placebo) and were analysed for safety by an Independent Data Monitoring Committee. Inclusion criteria for the patients were: age ≥18 years, prior (partial or total) nephrectomy of primary renal cell carcinoma with documented clear cell histology, no evidence of macroscopic and microscopic residual disease. Patients should have one of the following High Risk Group (RG) (referring to TNM classification, 6th edition UICC, 2002):

RG I: T3aN0/XM0 or T3bN0/XM0 or T3cN0/XM0 or T4N0/XM0

RG II: any T stage and N+ disease and M0

RG III: T1bN0/XM0 or T2N0/XM0, each with grading G 3 (Fuhrman or any other nuclear grading system with at least 3 grades), not more than 12 weeks between date of nephrectomy and randomisation, ECOG of 0 to 1.

Study Medication:

Girentuximab (cG250; an IgG1 kappa light chain chimeric version of an original murine monoclonal antibody mG250) was applied in a single loading dose of 50 mg (week 1) followed by weekly infusions of 20 mg of girentuximab (weeks 2-24). The drug was diluted in 100 ml normal saline (0.9% sterile sodium chloride in water) and was applied by intravenous infusion over 15 minutes. The placebo group received phosphate-buffered saline with polysorbate 20 (Tween® 20) without active ingredient. Duration of treatment was 24 weeks.

Immunohistochemistry:

Paraffin embedded nephrectomized tissue specimens were cut into section of 3-5 μm and collected on respective adhesive slides. Deparaffinisation and dehydration was done with EZ Prep mixture from Ventana Medical Systems, Inc. The tissue material was blocked and stained with a solution of the diluted antibody (CAIX M75, 1:150). The antibody was detected using a biotinylated IgG anti-mouse IgG antibody (Ventana Medical Systems, Inc.) followed by conjugated streptavidin horseradish peroxidase (Ventana Medical Systems, Inc.). The signal detection was done with diaminobenzidine and hydrogen peroxide (Ventana Medical Systems, Inc.). Positive and negative tissue controls were included as a reference.

Statistical Methods:

The efficacy evaluation was primarily analysed for the Intent-to-treat (ITT) population consisting of all 864 patients randomised. In addition the analysis was repeated for the Per Protocol (PP) Population consisting of 766 patients. Patients who received at least eight consecutive administrations of study medication (week 1 to 8) and had no major protocol deviation as defined in the deviation criteria prior to unblinding were evaluated as Per Protocol (PP) Population.

The sample size calculation was performed using the program Pass 2002. Statistical summaries were produced using SAS® software version 8.1 or higher. For the efficacy analysis, incomplete/partial dates were imputed; missing safety dates were not imputed. Adverse events and medical histories were coded using the Medical Dictionary for Regulatory Activities; medications were coded using the World Health Organisation Drug Dictionary. The primary efficacy analysis was based on the Intent-to-treat (ITT) Population and was repeated using the Per Protocol Population.

Continuous variables were described using: number of observations, arithmetic mean, standard deviation, minimum, median and maximum. Categorical variables were presented using the number of observations and percentages. Hierarchical testing was applied for DFS and OS to keep the global significance level to ≤5% for both. Both DFS and OS were compared between the girentuximab arm and the placebo arm using the log-rank test and the Kaplan-Meier method. The significance levels for OS were adjusted using the O'Brien-Fleming approach for group sequential methods with an overall significance level of 5%. 95% confidence intervals for proportions were calculated using the exact method (Pearson-Clopper).

The potential effect of prognostic factors on both DFS and OS was investigated using the Cox proportional hazards model. The hazard ratio (girentuximab treatment versus placebo) was estimated together with its associated 95% confidence interval and p-value using a proportional hazards model.

Summary of Results:

At the time of the cut-off for data analysis 360 patients (41.7%) had experienced a DFS event and 504 (58.3%) were still without disease according to local investigator assessment. 0.6% of the DFS patients were locally assessed as having metastatic disease at baseline. Overall 181 patients had died. After the IRRC central reading assessment, a DFS event could be assigned for 389 patients (45%) whereas a censor date could be assigned for the remaining 475 (55%) patients. The number of DES events (293 excluding patients with metastatic disease at baseline) that occurred in the ITT population was comparable between the treatment arms (cG250: 142, 32.8%; Placebo: 151, 35.0%), as was the rate of metastases at baseline (DFS=0), seen in 11.5% of girentuximab patients and 10.7% of placebo patients.

The primary analysis for DFS based on the IRRC evaluation for the ITT population showed no statistically significant difference in overall median DFS between the treatment arms (hazard ratio [HR]=0.999, p=0.737). The median DFS for girentuximab was 71.4 months and the median DFS for the placebo group was not reached.

There was no statistically significant difference in DFS between treatment arms, regardless of High Risk Group (RG) classification (RG I: HR=0.934, p=0.596; RG II: HR=1.73, p=0.084; RG III: HR=0.984, p=0.627).

In addition, exploratory analyses done using a classification based on the CAIX antigen expression alone according to Bui et al. (Bui et al., Clinical Cancer Research 2003, 9: 802-811) have not delivered statistical significant results neither for the prognosis nor for the treatment effect. However, surprisingly the combination of the CAIX antigen expression with the intensity of the staining, the CAIX score, which can be considered as a measure of the antigen density, showed significant results for the treatment effect as well as for the prognosis.

Multivariate analysis for the CAIX score cut-offs (1.91 for ITT and 1.52 for ITT Placebo) derived from survival tree analyses show that the CAIX score is a prognostic, but not independent factor for prognosis in DFS ITT, OS ITT and OS Placebo. The results suggest the CAIX score cut-off of 1.52 (ITT Placebo) may be useful for prognosis.

For patients with a low CAIX score the Kaplan-Meier-Curves for the different treatment arms overlap independently of the cut-off used. This clearly shows that patients with a low CAIX score do not benefit from treatment.

Figure 1:
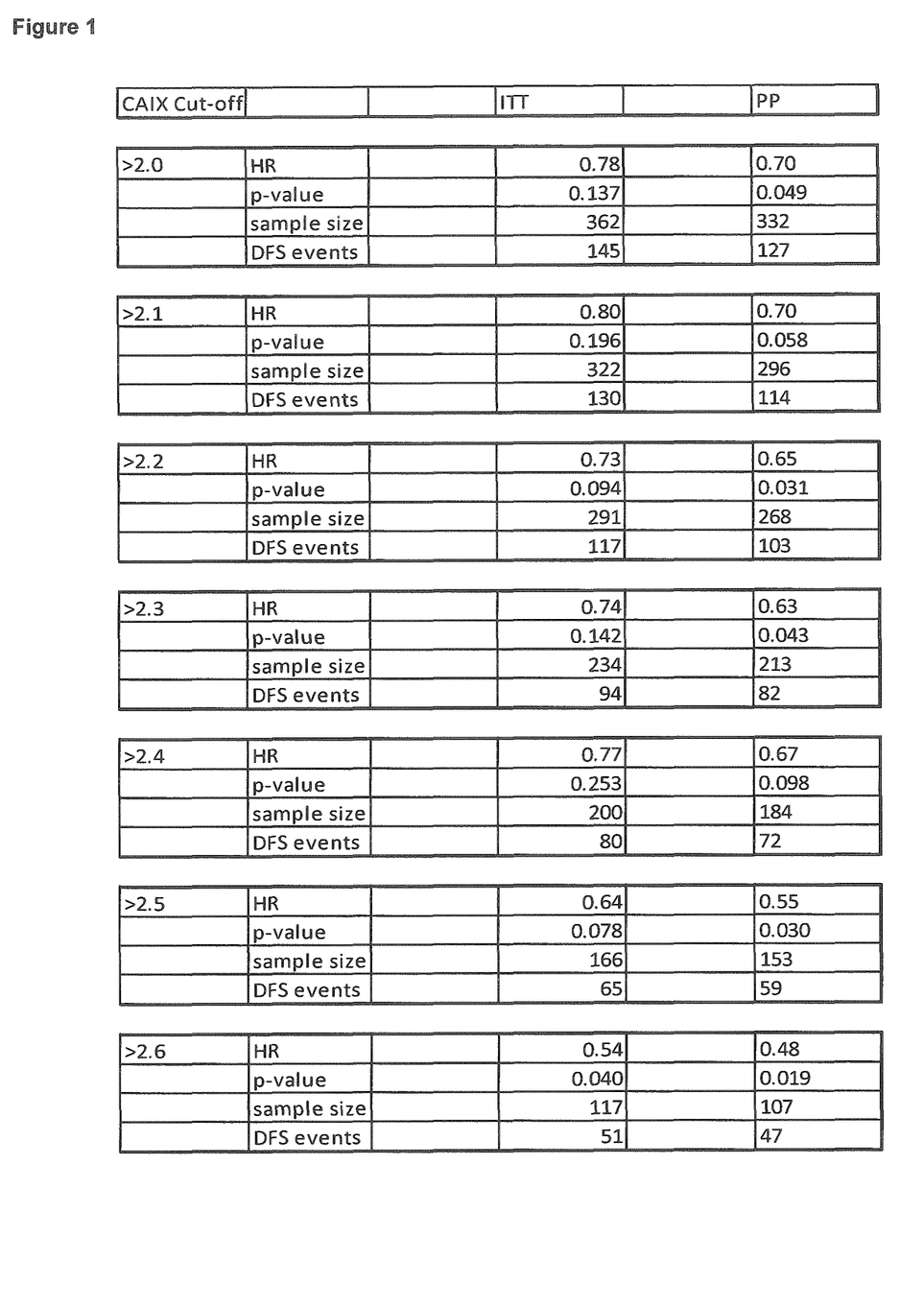
FIG. 1: HR (hazard ratio) and p-values for increasing CAIX-score values for the ITT (intended to treat) and PP populations (per protocol population)

A high CAIX score of ≥1.91 showed a positive trend for the treatment effect (HR=0.879, p-value 0.248). Subgroup analyses for all CAIX scores from 0.0 to 3.0 revealed that as the CAIX score increases, the more significant the treatment effect becomes (FIG. 1).

Figure 2:
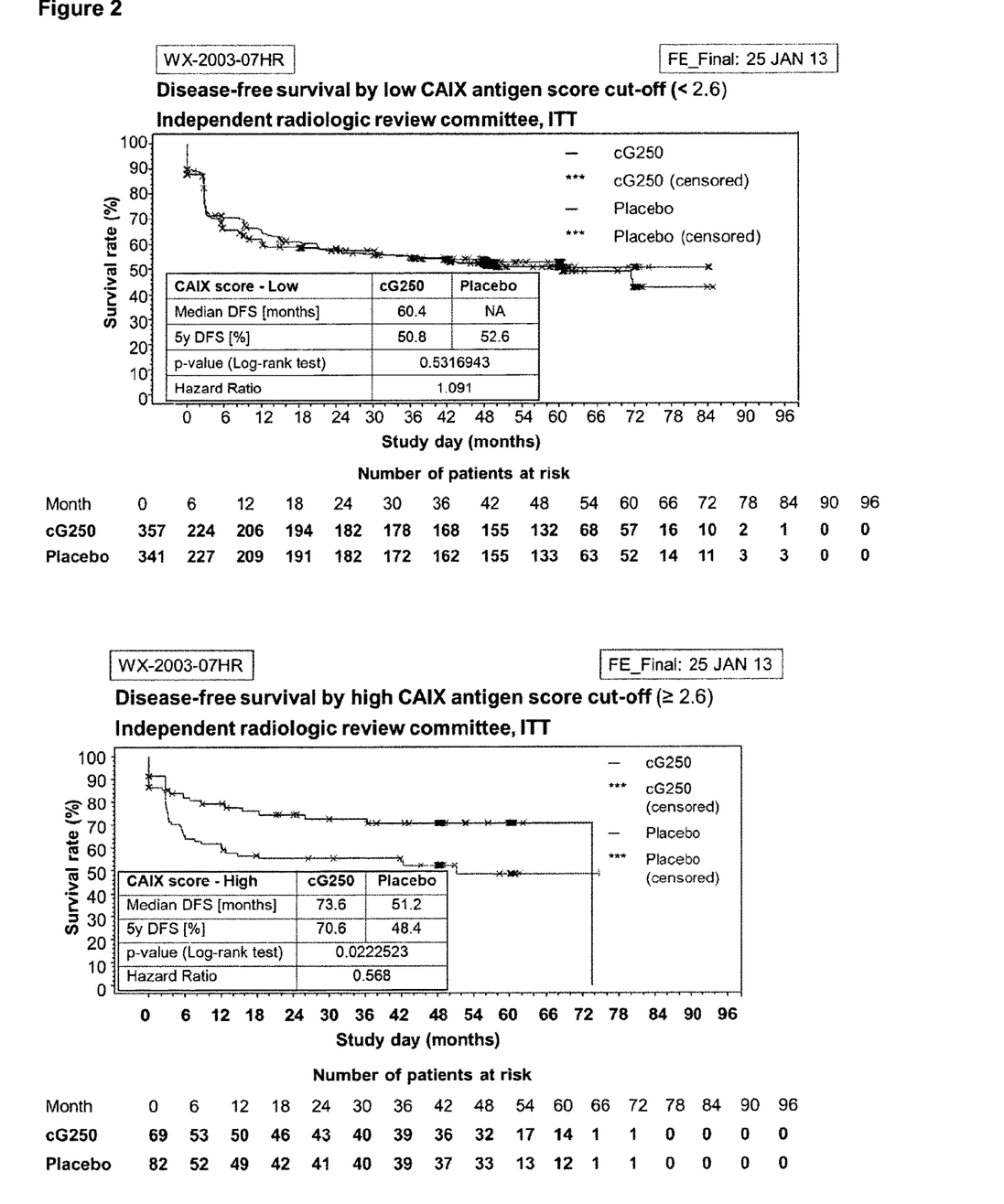
FIG. 2: DFS by treatment arm (cG250 vs. Placebo) for CAIX cut-off of 2.6

A CAIX score of ≥2.6 results in a statistically significant treatment effect with median DFS increasing from 51.2 months in the placebo arm to 73.6 months in cG250 patients (17% of the whole patient population, HR=0.568; p=0.022; FIG. 2). The 151 patients in the ITT population with a high CAIX score of ≥2.6 were evenly distributed between the cG250 and the placebo arm. Interestingly, patients in the placebo arm showed a 5 year DFS time (48.4 months versus 51.7 months) similar to patients with a CAIX score <2.6 regardless of treatment arm. Adjusting the population for patients with metastasis at baseline or for patients with positive lymph nodes did not change the outcome. Taking the PP population with a CAIX score ≥2.6 (N=139) improved both the hazard ratio and the significance level (HR=0.508; p=0.007; FIG. 2).

Figure 3:
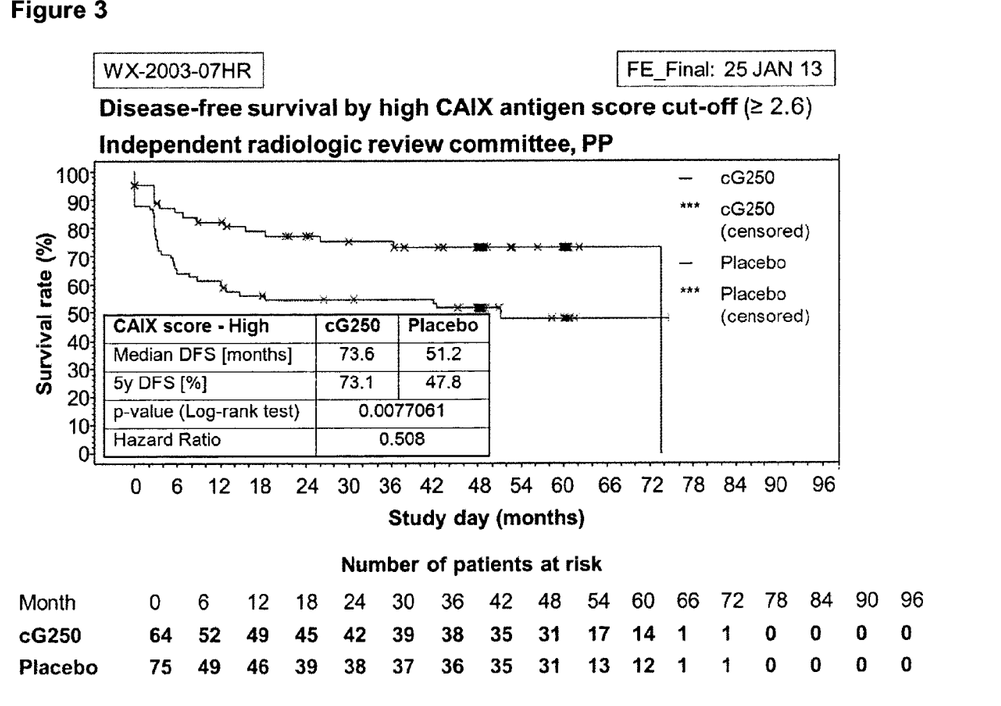
FIG. 3: DFS curve for PP population with CAIX scores ≥2.6

Overall, the outcomes seen in the ITT population were reflected by the outcomes in the PP population (FIG. 3).

Figure 4:
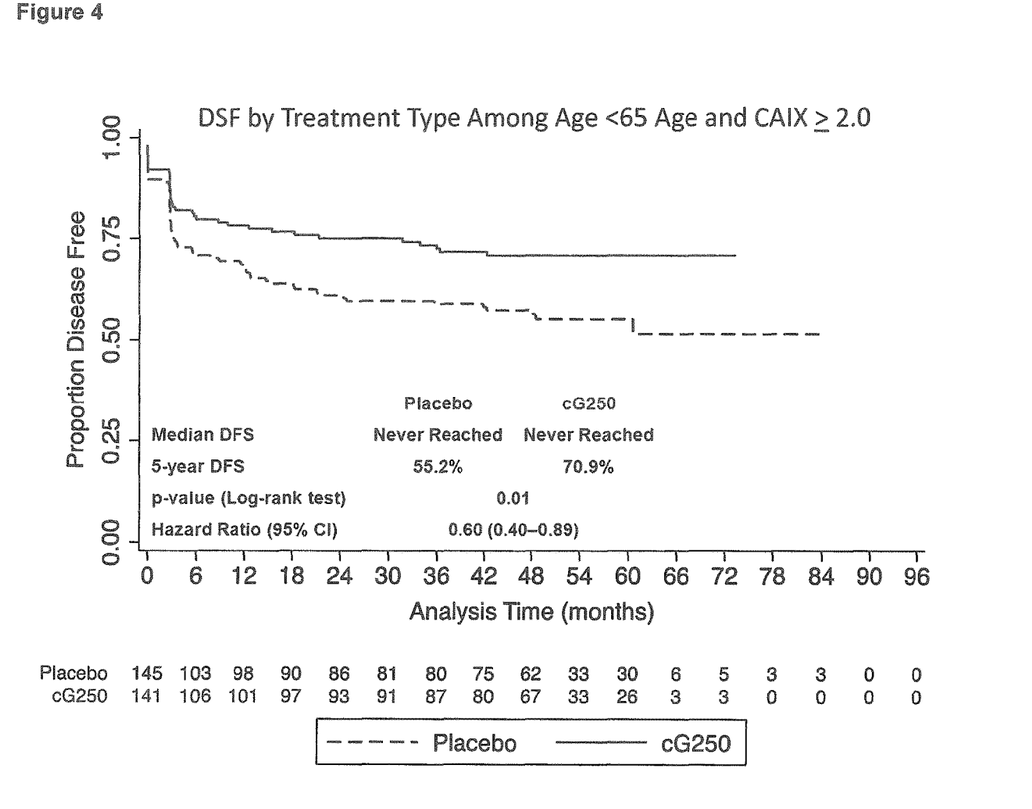
FIG. 4: High CAIX Score (≥2.0) and Age <65 years (ITT population)

A further subgroup analysis revealed a statistically significant treatment effect with median DFS increasing from 55.2 months in the placebo arm to 70.9 months in cG250 patients with a CAIX score of ≥2.0 and <65 years (HR=0.60; 95% CI 0.40-0.89; p-value=0.01; FIG. 4).

In addition, the analyses have shown that clear cell RCC patients with a high T-stage (T3/T4), a low Grading (G1/G2), no lymph node involvement (N0/NX) and no metastatic disease have a significantly worse prognosis with a low CAIX score as compared to patients with a high CAIX score.

tumor sample, by quantifying the expression of CAIX protein in said reference tumor sample in vitro by tumor cell staining, wherein a linear increase in staining of said reference tumor sample is determined and stained cells are divided into three groups of increasing staining wherein the respective increase in staining is the same for each group, wherein a fourth group has no staining and wherein said specific tumor cells are the same type of tumor cells as in said cancer sample, (c) quantifying the expression of CAIX protein in said cancer sample in vitro by tumor cell staining and determining a CAIX score by the formula: CAIX Score=(0×percentage of viable tumor cells with no staining)+(1×percentage of viable tumor cells with faint staining)+(2×percentage of viable tumor cells with moderate staining)+(3×percentage of viable tumor cells with strong staining), wherein faint staining, moderate staining and strong staining are the three groups with increasing staining determined based on said score system in (b), and wherein said tumor cells in said cancer sample are stained using the same specific staining agent as used in step (b), (d) comparing the CAIX Score with a predetermined threshold value of 2.0, (e) classifying the cancer disease as susceptible to treatment with a CAIX targeting compound if the CAIX score is 2.0, and (f) administering a CAIX targeting compound to said cancer patient classified as susceptible to treatment with a CAIX targeting compound, wherein said CAIX targeting compound is an anti-CAIX antibody or a functional fragment thereof which comprises the same six CDRs as the full length anti-CAIX antibody girentuximab.

The invention claimed is:

1. A method for classifying and treating a cancer disease comprising
   (a) obtaining a cancer sample from a cancer patient diagnosed with a non-metastatic type of cancer,
   (b) obtaining or establishing a score system for a specific staining agent and specific tumor cells using a reference 2. The method according to claim 1, wherein said CAIX targeting compound is the anti-CAIX antibody comprising the same six CDRs as the full length anti-CAIX antibody girentuximab.

3. The method for classifying and treating a cancer disease according to claim 1, wherein the cancer is renal clear cell carcinoma.

4. The method according to claim 1, wherein said anti-CAIX antibody is chimeric G250 antibody or humanized G250 antibody.

5. The method according to claim 4, wherein said chimeric G250 antibody is girentuximab.

6. The method according to claim 1, wherein said CAIX targeting compound is the functional fragment comprises the same six CDRs as the full-length anti-CAIX antibody girentuximab.

* * * * *